United States Patent [19]
Conrow et al.

[11] Patent Number: 5,929,111
[45] Date of Patent: Jul. 27, 1999

[54] A-SECO STEROIDS EFFECTIVE AT TREATING OPHTHALMIC PATHOLOGICAL NEOVASCULARIZATION AND CONTROLLING INTRAOCULAR PRESSURE

[75] Inventors: Raymond E. Conrow, Crowley; Abbot F. Clark, Arlington, both of Tex.

[73] Assignee: Alcon Laboratories, Inc., Fort Worth, Tex.

[21] Appl. No.: 08/992,418

[22] Filed: Dec. 17, 1997

Related U.S. Application Data

[60] Provisional application No. 60/032,491, Dec. 18, 1996.

[51] Int. Cl.$^6$ .......................... A61K 31/215; A61K 31/58; A61K 31/585; A61K 31/19
[52] U.S. Cl. .......................... 514/529; 514/174; 514/175; 514/557
[58] Field of Search .................................. 514/557, 174, 514/175, 529

[56] References Cited

U.S. PATENT DOCUMENTS

| | | |
|---|---|---|
| 2,951,074 | 8/1960 | Chemerda et al. . |
| 4,052,422 | 10/1977 | Cimarusti . |
| 4,550,022 | 10/1985 | Garabedian et al. . |
| 4,771,042 | 9/1988 | Braughler et al. ........................ 514/171 |
| 4,863,912 | 9/1989 | Southren et al. ........................ 514/177 |
| 4,945,089 | 7/1990 | Clark ........................................ 514/171 |

FOREIGN PATENT DOCUMENTS

| | | |
|---|---|---|
| WO 87/02672 | 5/1987 | WIPO . |
| WO 91/03245 | 3/1991 | WIPO . |

OTHER PUBLICATIONS

A. Abad, Silica Gel Catalyzed Eschenmoser Reactioin, *Synlett*, pp. 787–788 (1991).
Ashino–Fuse, et al., Medroxyprogesterone Acetate, An Anti– Cancer And Anti–Angiogenic Steroid, Inhibits The Plasminogen Activator In Bovine Endothelial Cells, *Int. J. Cancer*, vol. 44, pp. 859–864 (1989).
BenEzra, Neovasculogenic Ability of Prostaglandins, Growth Factors, and Synthetic Chemoattractants, *American Journal of Ophthalmology*, vol. 86, No. 4, pp. 455–461, (1978).
Cantrill, et al., Comparison of In Vitro Potency of Corticosteroids with Ability to Raise Intraocular Pressure, *Am. J. Opthal.*, vol.. 79, No. 6, pp. 1012–1016 (1975).
Cariou, et al., Inhibition of Human Endothelial Cell Proliferation by Heparin and Steroids, *Cell Biology International Reports*, vol. 12, No. 12, pp. 1037–1047 (Dec., 1988).
Cella, J.A., A Convenient Procedure For Preparative Scale Oxidation Of Enones, *Synthetic Communications*, vol. 13(2), pp. 93–98 (1983).
Clark, Steroids, Ocular Hypertension and Glaucoma, *J. Glaucoma*, vol. 4, pp. 354–369 (1995).
Crum, et al., A New Class of Steroids Inhibits Angiogenesis in the Presence of Heparin or a Heparin Fragment, *Science*, vol. 230, pp. 1375–1378 (1985).

Djerassi, et al., Selective Reduction Of Steroids by Homogeneous Catalytic Hydrogenation, *J. Am. Chem. Soc.*, vol. 88, pp. 4537–4538 (1966).
Folkman, et al., Angiogenic Factors, *Science*, vol. 235, pp. 442–447 (1987).
Folkman, et al., Angiogstatic Steroids, *Ann. Surg.*, vol. 206, No. 3, pp. 374–382 (1987).
Furcht, Critical Factors Controlling Angiogenesis: Cell Products, Cell Matrix, and Growth Factors, *Laboratory Investigation*, vol. 55, No. 5, pp. 505–509 (1986).
Ingber, et al., A Possible Mechanism for Inhibition of Angiogenesis by Angiostatic Steroids: Induction of Capillary Basement Membrane Dissolution, *Endocrinology*, vol. 119, No. 4, pp. 1768–1775 (1986).
Johnson, et al., Glaucoma: An Overview, *Mayo Clin. Proc*, vol. 61, pp. 59–67 (1986).
Kitazawa, Increased Intraocular Pressure Induced by Corticosteroids, *American Journal Of Ophthalmology*, vol. 82, No. 3, pp. 492–495 (1976).
Knepper, et al., Glycosaminoglycans and Outflow Pathways of the Eye and Brain, *Pediatric Neuroscience*, vol. 12, pp. 240–251 1986.
Li, et al., Angiostatic Steroids Potentiated by Sulphated Cyclodextrin Inhibit Corneal Neovascularization, *Investigative Ophthalmology and Visual Science*, vol. 32, No. 11, pp. 2898–2905 (1991).
Maragoudakis, et al., Antiangiogenic Action of Heparin Plus Cortisone is Associated with Decreased Collagenous Protein Synthesis in the Chick Chorioallantoic Membrane System, *The Journal of Pharmacology and Experimental Therapeutics*, vol. 251, No. 2, pp. 679–682 (1989).
Milewich, et al., *Organic Syntheses*, Collective vol. VI, p. 690 (1988).
Mindel, et al., Comparative Ocular Pressure Elevation by Medrysone, Fluorometholone, and Dexamethasone Phosphate, *Arch. Ophthalmol.*, vol. 98, pp. 1577–1578 (1980).
Rohen, Why is Intraocular Pressure Elevated in Chronic Simple Galucoma?, *American Academy of Ophthalmology*, vol. 90, No. 7, pp. 758–765 (1983).
Southren, et al., Intraocular Hypotensive Effect of a Topically Applied Cortisol Metabolite, Tetrahydrocortisol, *Investigative Ophthalmology and Visual Science*, vol. 28 (May, 1987).
Takeda, et al., *J. Am. Chem. Soc.*, vol. 105, pp. 563–568 (1983).
Tokida, et al., Production of Two Variant Laminin Forms by Endothelial Cells and Shift of Their Relative Levels by Angiostatic Steroids, *The Journal of Biological Chemistry*, vol. 264, No. 30, pp. 18123–18129 (1990).
Wieland, et al., *Helvetica Chemica Acta*, vol. 50, pp. 2108–2110 (1967).

*Primary Examiner*—William R. A. Jarvis
*Attorney, Agent, or Firm*—Michael C. Mayo

[57] ABSTRACT

A-seco steroids are disclosed. Methods of use are disclosed for treating ophthalmic pathological neovascularization and controlling intraocular pressure.

7 Claims, No Drawings

A-SECO STEROIDS EFFECTIVE AT TREATING OPHTHALMIC PATHOLOGICAL NEOVASCULARIZATION AND CONTROLLING INTRAOCULAR PRESSURE

Priority is claimed from the provisional application, U.S. patent application Serial No. 60/032,491, filed Dec. 18, 1996.

BACKGROUND OF THE INVENTION

This invention relates to A-seco steroids. The compounds are also useful in preventing and treating neovascularization and may also be used to control ocular hypertension. Specifically, the invention is directed to A-seco steroids, pharmaceutical compositions comprising the A-seco steroids, and methods of treatment which comprise administering these compositions to treat ocular hypertension, including controlling ocular hypertension associated with primary open angle glaucoma, and to treat neovascularization. In addition, the compounds can be used in combination with glucocorticoids to treat ocular inflammation without the significant intraocular pressure rise commonly associated with the use of glucocorticoids.

Steroids functioning to inhibit angiogenesis in the presence of heparin or specific heparin fragments are disclosed in Crum, et al., *A New Class of Steroids Inhibits Angiogenesis in the Presence of Heparin or a Heparin Fragment*, Science, Vol. 230, pp. 1375–1378 (Dec. 20, 1985). The authors refer to such steroids as "angiostatic" steroids. Included within the new class of steroids found to be angiostatic are the dihydro and tetrahydro metabolites of cortisol and cortexolone. In a follow-up study directed to testing a hypothesis as to the mechanism by which the steroids inhibit angiogenesis, it was shown that heparin/angiostatic steroid compositions cause dissolution of the basement membrane scaffolding to which anchorage dependent endothelia are attached resulting in capillary involution; see, Ingber, et al., *A Possible Mechanism for Inhibition of Angiogenesis by Angiostatic Steroids: Induction of Capillary Basement Membrane Dissolution*, Endocrinology, Vol. 119, pages 1768–1775 (1986). More recently, other theories regarding the mechanism of action of angiostatic steroids have developed. For example, angiostatic steroid induced inhibition of neovascularization may occur due to: inhibition of vascular endothelial cell proliferation, Cariou, et al., *Inhibition of Human Endothelial Cell Proliferation by Heparin and Steroids*, Cell Biology International Reports, Vol. 12, No. 12, pp. 1037–1047 (December, 1988); or inhibition of vascular endothelial cell plasminogen activator activity, Ashino-Fuse, et al., *Medroxyprogesterone Acetate, An Anti-Cancer and Anti-Angiogenic Steroid, Inhibits the Plasminogen Activator in Bovine Endothelial Cells*, Int. J. Cancer, 44, pp. 859–864 (1989).

A group of tetrahydro steroids useful in inhibiting angiogenesis is disclosed in International Patent Application No. PCT/US86/02189, Aristoff, et al., (The Upjohn Company). The compounds are disclosed for use in treating head trauma, spinal trauma, septic or traumatic shock, stroke and hemorrhage shock. In addition, the patent application discusses the utility of these compounds in embryo implantation and in the treatment of cancer, arthritis and arteriosclerosis. Some of the steroids disclosed in Aristoff et al. are disclosed in U.S. Pat. No. 4,771,042 in combination with heparin or a heparin fragment for inhibiting angiogenesis in a warm blooded animal.

Compositions of hydrocortisone, "tetrahydrocortisol-S," and U-72,745G, each in combination with a beta cyclodextrin, have been shown to inhibit corneal neovascularization: Li, et al., *Angiostatic Steroids Potentiated by Sulphated Cyclodextrin Inhibit Corneal Neovascularization*, Investigative Ophthalmology and Visual Science, Vol. 32, No. 11, pp. 2898–2905 (October, 1991). The steroids alone reduce neovascularization somewhat but are not effective alone in effecting regression of neovascularization.

Tetrahydrocortisol (THF) has been disclosed for its use in lowering the intraocular pressure ("IOP") of rabbits made hypertensive with dexamethasone alone, or with dexamethasone/5-beta-dihydrocortisol; see Southren, et al., *Intraocular Hypotensive Effect of a Topically Applied Cortisol Metabolite: 3-alpha, 5-beta-tetrahydrocortisol*, Investigative Ophthalmology and Visual Science, Vol. 28 (May, 1987). The authors suggest THF may be useful as an antiglaucoma agent. In U.S. Pat. No. 4,863,912, issued to Southren et al. on Sep. 5, 1989, pharmaceutical compositions containing THF and a method for using these compositions to control intraocular pressure are disclosed. THF has been disclosed as an angiostatic steroid in Folkman, et al., *Angiostatic Steroids*, Ann. Surg., Vol. 206, No. 3 (1987) wherein it is suggested angiostatic steroids may have potential use for diseases dominated by abnormal neovascularization, including diabetic retinopathy, neovascular glaucoma and retrolental fibroplasia.

Many compounds classified as glucocorticoids, such as dexamethasone and prednisolone, are very effective in the treatment of inflamed tissues; however, when these compounds are administered systemically or topically applied to the eye to treat ocular inflammation, certain patients experience elevated intraocular pressure. Patients who experience these elevations when treated with glucocorticoids are generally referred to as "steroid responders." These pressure elevations are of particular concern to patients who already suffer from elevated intraocular pressures, such as glaucoma patients. In addition, there is always a risk that the use of glucocorticoids in patients having normal intraocular pressures will cause pressure rises great enough to damage ocular tissues. Since glucocorticoid therapy is frequently long term (i.e., several days or more), there is potential for significant damage to ocular tissue as a result of prolonged elevations in intraocular pressure attributable to that therapy.

The following articles may be referenced for further background information concerning the well-recognized association between ophthalmic glucocorticoid therapy and elevations in intraocular pressure:

Kitazawa, *Increased Intraocular Pressure Induced by Corticosteroids*, Am. J. Ophthal., Vol. 82, pp. 492–493 (1976);

Cantrill, et al., *Comparison of In Vitro Potency of Corticosteroids with Ability to Raise Intraocular Pressure*, Am. J. Ophthal., Vol. 79, pp. 1012–1016 (1975);

Mindel, et al., *Comparative Ocular Pressure Elevation by Medrysone, Fluorometholone, and Dexamethasone Phosphate*, Arch. Ophthal., Vol. 98, pp. 1577–1578 (1980); and Clark, *Steroids, Ocular Hypertension and Glaucoma*, J. Glaucoma, Vol. 4, pp. 354–369 (1995).

Commonly assigned U.S. Pat. No. 4,945,089 discloses the use of the angiostatic steroid tetrahydrocortexolone in combination with a glucocorticoid to treat ocular inflammation without the intraocular pressure elevating effect commonly associated with topical administration of glucocorticoids. In addition, commonly assigned International Publication No. WO 91/03245 discloses the angiostatic steroids of Aristoff, et al. in combination with glucocorticoids to treat ocular inflammation without significant increase in intraocular pressure.

SUMMARY OF THE INVENTION

This invention is directed to A-seco steroids and methods of using compositions of these steroids in inhibiting neovascularization. The compositions containing the steroids can be used for treatment of angiogenesis dependent diseases, for example: head trauma, spinal trauma, septic or traumatic shock, stroke, hemorrhagic shock, cancer, arthritis, arteriosclerosis, angiofibroma, arteriovenous malformations, corneal graft neovascularization, delayed wound healing, diabetic retinopathy, granulations, burns, hemangioma, hemophilic joints, hypertrophic scars, neovascular glaucoma, nonunion fractures, Osler-Weber Syndrome, psoriasis, pyogenic granuloma, retrolental fibroplasia, pterigium, scleroderma, trachoma, vascular adhesions, and solid tumor growth. In particular, the A-seco steroids and compositions thereof are useful for controlling ocular neovascularization.

The invention also encompasses methods for controlling ocular hypertension and glaucoma through the systemic or local administration of the compositions disclosed herein.

The present invention also includes the use of the A-seco steroids in combination with glucocorticoids for the treatment of ocular inflammation. The addition of at least one A-seco steroid makes it possible to employ the potent antiinflammatory glucocorticoids without producing significant elevations in intraocular pressure.

DETAILED DESCRIPTION OF THE INVENTION

The development of blood vessels for the purpose of sustaining viable tissue is known as angiogenesis or neovascularization. Agents which inhibit neovascularization are known by a variety of terms such as angiostatic, angiolytic or angiotropic agents. For purposes of this specification, the term "angiostatic agent" means compounds which can be used to control, prevent, or inhibit angiogenesis.

There is currently no effective method for controlling the neovascularization in angiogenesis-dependent diseases. In particular, ocular neovascularization has not been successfully treated in the past. Neovascularization of tissues in the front of the eye (i.e. the cornea, iris, and the trabecular meshwork) and other conditions, including conditions in the back of the eye, for example, retinal, subretinal, macular, and optical nerve head neovascularization, can be prevented and treated by administration of the A-seco steroids of this invention. The A-seco steroids of the present invention are useful in preventing and treating neovascularization, including providing for the regression of neovascularization.

The A-seco steroids can also be used for the control of ocular hypertension. In particular, the agents can be used for the treatment of primary open angle glaucoma.

The A-seco steroids of the present invention are of the following formula (I):

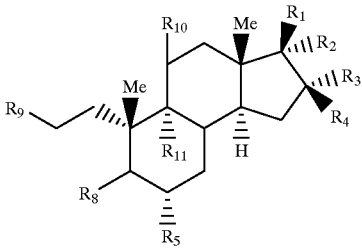

wherein:
$R_1$ is OH, OC(=O)$R_7$, $R_7$, C(=O)$R_7$, or C(=O)CH$_2$OR$_6$;
R2 is H, OH, OC(=O)$R_7$, CH$_3$, CH$_2$CH$_3$, C≡CH, or $R_2$ is combined with $R_3$ to form a cyclic acetonide;
$R_3$ is H, CH$_3$, OH, OC(=O)$R_7$, or $R_3$ may be combined with $R_2$ to form a cyclic acetonide;
$R_4$ is H or CH$_3$, with the proviso that if R4 is CH$_3$ then $R_3$ is H;
$R_5$ is H, F or CH$_3$;
$R_6$ is H, C(=O)$R_7$, P(=O)(OH)$_2$ or a salt thereof;
$R_7$ is $C_1$ to $C_8$ alkyl, branched alkyl, cycloalkyl, or haloalkyl;
$R_8$ is (=O), OH or OC(=O)$R_7$ and may be in the α or β configuration, or $R_8$ may be combined with $R_9$ to form a lactone;
$R_9$ is C≡CH, C(=O)CH$_3$, COOH, COOR$_7$, CH$_2$OH, CH$_2$OC(=O)$R_7$, CONH$_2$, CONHR$_7$, CONR$_7$R$_7$, or $R_9$ may be combined with $R_8$ to form a lactone;
$R_{10}$ is H, (=O) or OH, or OC(=O)$R_7$ which may be in the α or β configuration, or may be combined with $R_{11}$ to form a double bond; and
$R_{11}$ is H, Cl, F, or may be combined with $R_{10}$ to form a double bond.

Some of the compounds contained within formula (I) are believed to be novel. Compounds with the following substituents are preferred:
$R_1$ is C(=O)CH$_2$OR$_6$;
$R_2$ is OH;
$R_3$ is H;
$R_4$ is H;
$R_5$ is H;
$R_6$ is C(=O)$R_7$;
$R_7$ is CH$_3$;
$R_8$ is (=O);
$R_9$ is COOR$_7$;
$R_{10}$ is OH and in the β configuration or with $R_{11}$ forms a double bond; and
$R_{11}$ is H, or combined with $R_{10}$ forms a double bond.

The starting materials for the preparation of the A-seco steroids of formula (I) are $\Delta^4$-3-keto steroids, which are commercially available (for example, from Steraloids, Inc., Wilton, N.H., USA), or can be prepared by methods known to those skilled in the art, e.g., by selective hydrogenation of a $\Delta^{1,4}$-3-keto steroid (see, C. Djerassi and *J. Gutzwiller, J. Am. Chem. Soc.,* vol. 88, p. 4537 (1966). The following discussion describes various synthetic approaches to preparing A-seco steroids of the present invention, wherein references to "R" groups are relative to formula (I), above.

Some of the A-seco steroids may be prepared by oxidative cleavage of $\Delta^4$-3-keto steroids, which also results in concomitant excision of carbon 4. This can be accomplished by various methods, depending on the substituents present in the $\Delta^4$-3-keto steroid starting material, as would be apparent to one skilled in the art. For example, L. Milewich and L. R. Axelrod, *Organic Syntheses, Collective Volume* VI, p. 690 (1988), describe the reaction of testosterone acetate with sodium periodate and potassium permanganate to give a compound wherein $R_1$ is $OC(=O)CH_3$, $R_2$, $R_3$, $R_4$, $R_5$, $R_{10}$, and $R_{11}$ are H, $R_8$ is (=O), and $R_9$ is COOH. U.S. Pat. No. 2,951,074 (Chemerda et al.), teaches the sequence: (1) protection of hydrocortisone as its 17,20:20,21-bismethylenedioxy (BMD) derivative, (2) ozonolysis of the resulting BMD-protected steroid (with concomitant loss of C-4), and (3) removal of the BMD group to give a compound wherein $R_1$ is $C(=O)CH_2OH$, $R_2$ is OH, $R_3$, $R_4$, $R_5$, and $R_{11}$ are H, $R_8$ is (=O), $R_{10}$ is β-OH and $R_9$ is COOH. J. A. Cella, *Synthetic Communications*, vol. 13, p. 93 (1983), describes the ozonolysis of progesterone to give the compound wherein $R_1$ is $C(=O)CH_3$, $R_2$, $R_3$, $R_4$, $R_5$, $R_{10}$, and $R_{11}$ are H, $R_8$ is (=O), and $R_9$ is COOH. This reference also describes the ozonolysis of cholestenone to give the compound wherein $R_1$ is $CH(CH_3)CH_2CH_2CH_2CH(CH_3)_2$, $R_2$, $R_3$, $R_4$, $R_5$, $R_{10}$, and $R_{11}$ are H, $R_8$ is (=O), and $R_9$ is COOH.

Other A-seco steroids may be prepared from $\Delta^4$-3-keto steroids by employing the "Tanabe-Eschenmoser fragmentation," see, A. Abad, *Synlett*, p. 787 (1991) and cited references. Abad describes the sequence of epoxidation of testosterone acetate followed by formation and then fragmentation of the tosylhydrazone derivative to give the product wherein $R_1$ is $OC(=O)CH_3$, $R_2$, $R_3$, $R_4$, $R_5$, $R_{10}$, and $R_{11}$ are H, $R_8$ is (=O), and $R_9$ is C≡CH. Ahad describes a similar sequence, starting with 17α-hydroxyprogesterone, which gives the product wherein $R_1$ is $C(=O)CH_3$, $R_2$ is OH, $R_3$, $R_4$, $R_5$, $R_{10}$, and $R_{11}$ are H, $R_8$ is (=O), and $R_9$ is C≡CH. P. Wieland, et al., *Helvetica Chemica Acta*, vol. 50, p. 2108 (1967), describe a similar sequence beginning with hydrocortisone-BMD to give a BMD-protected A-seco steroid, which upon removal of the BMD group (as above), yields the product wherein $R_1$ is $C(=O)CH_2OH$, $R_2$ is OH, $R_3$, $R_4$, $R_5$, and $R_{11}$ are H, $R_8$ is (=O), $R_{10}$ is β-OH and $R_9$ is C≡CH.

A novel method of A-seco steroid synthesis, as illustrated in Scheme I, and Examples 1 and 2, below, consists of vicinal dihydroxylation of the 4,5-double bond of a $\Delta^4$-3-keto steroid, yielding an intermediate 4,5-dihydroxy-3-keto steroid, followed by periodic acid treatment of the 4,5-dihydroxy-3-ketosteroid, to give the desired A-seco steroid.

Scheme 1

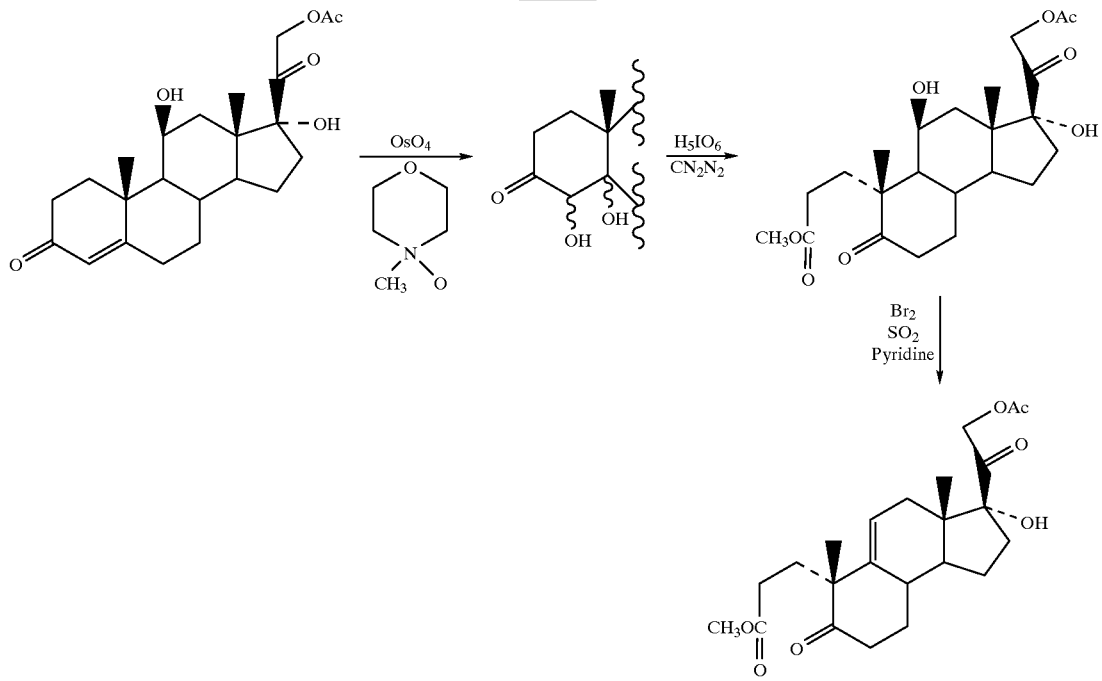

Further reactions which are known or apparent to those skilled in the art may be necessary in order to synthesize other A-seco steroids. For example, esterification and selective dehydration of the Example 1 intermediate yields the $\Delta^{9(11)}$ 3,5-seco-4-norcorticosteroid, wherein $R_1$ is $C(=O)CH_2OC(=O)CH_3$, $R_2$ is OH, $R_3$, $R_4$, $R_5$ are H, $R_8$ is (=O), $R_{10}$ and $R_{11}$ taken together form a double bond, and $R_9$ is $COOCH_3$. Reduction reactions may be performed on the intermediates or compounds of the present invention; for example, a mixed carboxylic-carbonic anhydride derivative of a compound wherein $R_9$ is COOH may be reduced to a compound wherein $R_9$ is $CH_2OH$. Amidation reactions may be performed on intermediates or compounds of the present invention; for example, a compound wherein $R_9$ is COOH may be amidated to yield a compound wherein $R_9$ is $CONH_2$, $CONHR_7$, or $CONR_7R_7$. Transformation reactions may also be performed; for example, a terminal acetylenic group, C≡CH, of an intermediate or compound of the present invention may be transformed to a methyl ketone $C(=O)CH_3$ (see for example, by the Hg(II)-promoted hydrolysis method of K. Takeda, et al., *J. Am. Chem. Soc.*, vol. 105, p. 563 (1983)).

The following are further synthesis examples of the A-seco steroid compounds of the present invention:

EXAMPLE 1

Preparation of Methyl A-seco-4-nor-21-acetoxy-11β, 17α-dihydroxypregnan-5, 20-dione-3-carboxylate The intermediate, 4, 5, 11β, 17α, 21-Pentahydroxypregnan-3, 20-dione-21-acetate, was first prepared. Osmium tetroxide (0.28 g, 1.1 mmol) was added to a stirred suspension of cortisol acetate (4.05 g, 10.0 mmol) and N-methylmorpholine-N-oxide (1.75 g, 15 mmol) in 50 mL of THF and 20 mL of water. After 46 hours, the reaction was quenched with 2M aqueous $Na_2S_2O_3$ and stirred for 15 minutes. The mixture was partitioned between EtOAc and water, the organic solution was washed with 1M aqueous $H_2SO_4$ (to pH 1), water (to pH 7), brine, and then dried ($MgSO_4$), eluted through Florisil with EtOAc, and concentrated to give 3.5 g (80%) of 4, 5, 11β, 17α, 21-Pentahydroxypregnan-3, 20-dione-21-acetate, as a white foam.

NMR (DMSO-$d_6$) δ 0.7 (br s, 3H), 1.10 (s, 3H); 1.0–2.2 (m); 2.06 and 2.07 (each s, total 3H); 4.1–5.5 (m, 8H).

$H_5IO_6$ (1.35 g, 5.9 mmol) was added to a stirred solution of 4, 5, 11β, 17α, 21-Pentahydroxypregnan-3, 20-dione-21-acetate (1.30 g, 3.0 mmol) in 15 mL of 1,4-dioxane and 5 mL of water. After 3.3 hours, the mixture was partitioned between EtOAc and water, the organic solution was washed with brine, and then dried ($MgSO_4$), filtered and concentrated. The residue was dissolved in $CH_2Cl_2$ (20 mL) and treated with excess ethereal $CH_2N_2$, followed after 10 minutes by HOAc quench. EtOAc was added and the organic solution extracted twice with aqueous $NaHCO_3$, with water and brine, and then dried ($MgSO_4$), filtered and concentrated. The residue was purified by flash chromatography (75 g silica, 55% EtOAc-hexanes) to give 0.42 g (26% from cortisol acetate) of methyl A-seco-4-nor-21-acetoxy-11β, 17α-dihydroxypregnan-5, 20-dione-3-carboxylate, as a foam.

NMR (DMSO-$d_6$) δ 0.78 (s, 3H); 1.25 (s, 3H); 1.0–2.8 (m); 2.10 (s, 3H); 2.25 (t, J=7, 1H); 3.58 (s, 3H); 4.13 (br s, 1H, H-11); 4.46 (d, J=4, 1H, xD20, OH-11); 4.9 (AB, 2H, J=17.6, Δv=70.4, H-21); 5.44 (s, 1H, xD20, OH-17).

EXAMPLE 2
Preparation of Methyl A-seco-4-nor-21-acetoxy-17α-hydroxypregn-9 (11)-en-5, 20-dione-3-carboxylate The method of Buss (U.S. Pat. No. 3,411,559) was employed. $SO_2$ gas (excess) was bubbled through 3 mL of dry pyridine at 0° C. under argon. A solution of methyl A-seco-4-nor-21-acetoxy-11β, 17α-dihydroxypregnan-5, 20-dione-3-carboxylate (0.39 g, 0.89 mmol) in 5 mL of dry $CH_2Cl_2$ was added with stirring, followed by dropwise addition of 0.05 mL (1.0 mmol) of $Br_2$. EtOAc was added and the solution extracted with water, 1M $H_2SO_4$, water (3x), brine, and then dried ($MgSO_4$), filtered and concentrated. Recrystallization from n-BuCl containing hexane afforded 0.12 g (32%) of methyl A-seco-4-nor-21-acetoxy-17α-hydroxypregn-9 (11)-en-5, 20-dione-3-carboxylate, m.p. 124.5–126.5° C. IR (KBr) v 3512 (sharp), 2952, 1728 (br, vs), 1456, 1439, 1408, 1370, 1273, 1232, 1202 $cm^{-1}$.

NMR (DMSO-$d_6$) δ 0.49 (s, 3H); 1.15 (s, 3H); 1.2–2.8 (m); 2.08 (s, 3H); 3.56 (s, 3H); 4.92 (AB, 2H, J=17.0, Δv=34.2, H-21); 5.49 (br d, J=5, H-1 1); 5.55 (s, 1H, xD20, OH-17).

Anal. calc'd: C, 65.69; H, 7.67.
Found: 65.58; 7.72.

The A-seco steroids of the present invention are useful in inhibiting pathological neovascularization in human patients. As used herein, the term "pathological neovascularization" refers to those conditions where the formation of blood vessels (neovascularization) is harmful to the patient. Examples of pathological neovascularization dependent diseases include: head trauma, spinal trauma, systemic or traumatic shock, stroke, hemorrhagic shock, cancer, arthritis, arteriosclerosis, angiofibroma, arteriovenous malformations, corneal graft neovascularization, delayed wound healing, diabetic retinopathy, granulations, burns, hemangioma, hemophilic joints, hypertrophic scars, neovascular glaucoma, nonunion fractures, Osler-Weber Syndrome, psoriasis, pyogenic granuloma, retrolental fibroplasia, pterigium, scleroderma, trachoma, vascular adhesions, and solid tumor growth.

In particular, the A-seco steroids are useful in preventing and treating any ocular neovascularization, including, but not limited to: retinal diseases (diabetic retinopathy, chronic glaucoma, retinal detachment, sickle cell retinopathy, senile macular degeneration due to subretinal neovascularization); rubeosis iritis; inflammatory diseases; chronic uveitis; neoplasms (retinoblastoma, pseudoglioma); Fuchs' heterochromic iridocyclitis; neovascular glaucoma; corneal neovascularization (inflammatory, transplantation, developmental hypoplasia of the iris); neovascularization resulting following a combined vitrectomy and lensectomy; vascular diseases (retinal ischemia, choroidal vascular insufficiency, choroidal thrombosis, carotid artery ischemia); pterigium; neovascularization of the optic nerve; and neovascularization due to penetration of the eye or contusive ocular injury.

Additionally the A-seco steroids are useful in treating pterygium (primary and recurrent), glaucoma filtration surgery bleb failure, hyperkeratosis, cheloid formation and polyp formation.

The initiation of new blood vessel formation may arise quite differently in various tissues or as a result of different diseases. Many substances have been found to induce neovascularization, see, Folkman, et al., *Angiogenic Factors, Science,* Volume 235, pp. 442–447 (1987). However, it is believed, that once initiated, the process of neovascularization is similar in all tissues regardless of the associated disease, Furcht, *Critical Factors Controlling Angiogenesis: Cell Products, Cell Matrix, and Growth Factors, Laboratory Investigation,* Volume 55, No. 5, pp. 505–509 (1986).

There are a variety of theories regarding the mechanism of action of angiostatic steroids. For example, angiostatic steroid induced inhibition of neovascularization may occur due to: dissolution of the capillary basement membrane, Ingber, et al., Supra; inhibition of vascular endothelial cell proliferation, Cariou, et al., *Inhibition of Human Endothelial Cell Proliferation by Heparin and Steroids, Cell Biology International Reports,* Vol. 12, No. 12, pp. 1037–1047 (December, 1988); effect on vascular endothelial cell laminin expression, Tokida, et al., *Production of Two Variant Laminin Forms by Endothelial Cells and Shift of Their Relative Levels by Angiostatic Steroids, The Journal of Biological Chemistry,* Vol. 264, No. 30, pp. 18123–18129 (Oct. 25, 1990); inhibition of vascular cell collagen synthesis, Maragoudakis, et al., *Antiangiogenic Action of Heparin Plus Cortisone is Associated with Decreased Collagenous Protein Synthesis in the Chick Chorioallantoic Membrane System, The Journal of Pharmacology and Experimental Therapeutics,* Vol. 251, No. 2, pp. 679–682 (1989); and inhibition of vascular endothelial cell plasminogen activator activity, Ashino-Fuse, et al., *Medroxyprogesterone Acetate, An Anti-Cancer and Anti-Angiogenic Steroid, Inhibits the Plasminogen Activator in Bovine Endothelial Cells,* Int. J. Cancer, 44, pp. 859–864 (1989).

There are many theories associated with the cause of neovascularization, and there may be different inducers depending on the disease or surgery involved, BenEzra, *Neovasculogenic Ability of Prostaglandins, Growth Factors, and Synthetic Chemoattractants, American Journal of Ophthalmology,* Volume 86, No. 4, pp. 455–461, (October, 1978). Regardless of the cause or the associated disease or surgery, it is believed that angiostatic agents work by inhibiting one or more steps in the process of neovascularization. Therefore, the A-seco steroids of this invention are useful in the treatment and prevention of neovascularization associated with a variety of diseases and surgical complications.

The use of the compositions of the present invention to ameliorate complications arising from glaucoma filtration surgery is a particularly important aspect of the invention. Glaucoma filtration surgery involves the surgical creation of a fistula with a conjuctival flap which allows the direct drainage of aqueous humor from the anterior chamber into the conjuctival tissue thereby lowering the elevated intraocular pressure associated with glaucoma. However, in many patients, the filtration "bleb" becomes scarred or healed over so that aqueous drainage can no longer occur. It has been noted that failing filtration blebs may become vascularized prior to failure. This vascularization may feed the fibroblasts which migrate, and proliferate, and block the bleb, or the vascularization itself may also result in physical blockage of the bleb. It is therefore likely that inhibition of filtration bleb neovascularization may inhibit filtration bleb failure.

Without intending to be bound by any theory, it is believed that the A-seco steroids of the type described above also act to control intraocular pressure by inhibiting the accumulation or stimulating the dissolution of amorphous extracellular material in the trabecular meshwork of the eye. The presence of this amorphous extracellular material alters the integrity of the healthy trabecular meshwork and is a symptom associated with primary open angle glaucoma (POAG). It is not well understood why this amorphous extracellular material builds up in the trabecular meshwork of persons suffering from POAG. However, it has been found that the amorphous extracellular material is generally composed of glycosaminoglycans (GAGs) and basement membrane material; see, *Ophthalmology,* Vol. 90, No. 7 (July 1983); *Mayo Clin. Proc,* Vol. 61, pp. 59–67 (Jan. 1986); and *Pediat. Neurosci.,* Vol. 12, pp. 240–251 (1985–86). When these materials build up in the trabecular meshwork, the aqueous humor, normally present in the anterior chamber of the eye, cannot leave this chamber through its normal route (the trabecular meshwork) at its normal rate. Therefore, a normal volume of aqueous humor is produced by the ciliary processes of the eye and introduced into the anterior chamber, but its exit through the trabecular meshwork is abnormally slow. This results in a buildup of pressure in the eye, ocular s hypertension, which can translate into pressure on the optic nerve. The ocular hypertension so generated can lead to blindness due to damage to the optic nerve.

Many methods for treating primary open angle glaucoma and ocular hypertension concentrate on blocking production of aqueous humor by the eye. However, aqueous humor is the fundamental source of nourishment for the tissues of the eye, particularly the cornea and lens which are not sustained by blood supply. Therefore, it is not desirable to deprive these tissues of the necessary irrigation and nutrition provided by the aqueous humor. It is desirable to strive for normal exit of the aqueous humor by maintaining the normal integrity of the trabecular meshwork. This is accomplished according to the present invention by the administration of A-seco steroids.

It is believed that the A-seco steroids disclosed herein function in the trabecular meshwork in a similar manner as shown by Ingber, et al., wherein it was shown that angiostatic steroids caused dissolution of the basement membrane scaffolding using a chick embryo neovascularization model; *Endocrinology,* Vol. 119, pp. 1768–1775 (1986). It is believed that the angiostatic steroids of the present invention prevent the accumulation, or promote the dissolution of, amorphous extracellular materials in the trabecular meshwork by inhibiting the formation of basement membrane materials and glycosaminoglycans. Thus, by preventing the development of these materials or promoting their dissolution, the normal integrity of the trabecular meshwork is retained and aqueous humor may flow through the trabecular meshwork at normal rates. As a result, the intraocular pressure of the eye is controlled.

The A-seco steroids may be contained in various types of pharmaceutical compositions, either together as a single composition or in separate compositions, in accordance with formulation techniques known to those skilled in the art. For example, the compounds may be included in tablets, capsules, solutions, suspensions and other dosage forms adapted for oral administration; solutions and suspensions adapted for parenteral use; solutions, suspensions or gels for topical ocular administration; solutions and suspensions adapted for intra-vitreal or intra-cameral use; and suppositories for rectal use. Solutions, suspensions and other dosage forms adapted for topical application to the involved tissues, such as tissue irrigating solutions, are particularly preferred for treatment of acute conditions associated with surgery or other forms of trauma.

The present invention is particularly directed to the provision of compositions adapted for treatment of ophthalmic tissues. Various types of vehicles may be used. The vehicles will generally be aqueous in nature. Aqueous solutions are generally preferred, based on ease of formulation, as well as a patient's ability to easily administer such compositions by means is of instilling one to two drops of the solutions in the affected eyes. However, the compounds of the present invention may also be readily incorporated into other types of compositions, such as suspensions, viscous or semi-viscous gels or other types of solid or semi-solid compositions. Suspensions may be preferred for compounds of the present invention which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0 percent by weight, based on the total weight of the composition (wt. %).

The route of administration (e.g., topical, parenteral or oral) and the dosage regimen will be determined by skilled clinicians, based on factors such as the exact nature of the condition being treated, the severity of the condition, the age and general physical condition of the patient, and so on.

As indicated above, use of compounds of the present invention to prevent or reduce angiogenesis in ophthalmic tissues is a particularly important aspect of the present invention. The compounds may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The compounds may also be used prophylactically, especially prior to ocular surgery or noninvasive ophthalmic procedures, or other types of surgery.

The use of physiologically balanced irrigating solutions as pharmaceutical vehicles for the A-seco steroids is preferred when the compositions are administered intraocularly. As used herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS® Sterile Irrigating Solution and BSS Plus® Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), the entire contents of which are hereby incorporated in the present specification by reference.

The specific type of formulation selected will depend on various factors, such as the compound or its salt being used, the dosage frequency, and the disease being treated. Topical aqueous solutions, suspensions, ointments, creams and gels are the preferred dosage forms for the treatment of pterygium, hyperkeratosis, and cheloid and polyp formation. Topical ophthalmic formulations are suitable for preventing glaucoma filtration bleb failure or scar formation associated with ophthalmic surgery.

In general, the doses used for the above described purposes will vary, but will be in an effective amount to inhibit or reduce neovascularization. As used herein, the term "effective is amount," is that amount of one or more A-seco steroids of the present invention which inhibits formation of new blood vessels or reduces the number of blood vessels which are involved in the pathological condition. The compounds will normally be contained in these formulations in an amount from about 0.01 to about 10.0 weight/percent. Preferable concentrations range from about 0.1 to about 5.0 weight/percent. Thus, for topical administration, these formulations are delivered to the disease site one to six times a day, depending on the routine discretion of the skilled clinician. Systemic administration, for example, in the form of tablets or suppositories is useful for the treatment of polyp formation. Tablets containing 10–1000 mg of a compound can be taken 2–3 times per day depending on the discretion of the skilled clinician.

In addition, antiinflammatory compositions of glucocorticoids can contain one or more A-seco steroids of the present invention. These compositions will contain one or more glucocorticoids in an antiinflammatory effective amount and will contain one or more angiostatic steroids of the present invention in an amount effective to inhibit the IOP elevating effect of the glucocorticoids. Preferred glucocorticoids are dexamethasone and prednisolone. The amount of each component will depend on various factors, such as the relative tendency of certain glucocorticoids to cause IOP elevations, the severity and type of ocular inflammation being treated, the estimated duration of the treatment, and so on. In general, the ratio of the amount of glucocorticoid to the amount of A-seco steroid on a weight to weight basis will be in the range of 10:1 to 1:20. The concentration of the glucocorticoid component will typically be in the range of about 0.01% to about 2.0% by weight. The concentration of the A-seco steroid will be in an amount effective to inhibit IOP elevation elicited by the glucocorticoids of the compositions of the present invention. As used herein, such an amount is referred to an "effective amount." In general, concentration of the A-seco steroid component will typically be is in the range of about 0.05% to about 5.0% by weight.

The compositions of the present invention are further illustrated by the following examples. The term "A-seco steroid" refers to any compound of the present invention, as described above.

EXAMPLE 4

Topical combination compositions useful for controlling ocular neovascularization:

| Component | wt. % |
| --- | --- |
| A-seco steroid | 0.005–5.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 5

A preferred topical composition useful for controlling neovascularzation:

| Component | wt. % |
| --- | --- |
| A-seco steroid | 0.005–5.0 |
| Tyloxapol | 0.01–0.05 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/HCl. The solution is then sterilized by means of filtration.

The A-seco steroids are sterilized by either dry heat or ethylene oxide. If ethylene oxide sterilization is selected, aeration for at least 72 hours at 50° C. is necessary. The sterilized angiostatic compound is weighed aseptically and placed into a pressurized ballmill container. The tyloxapol, in sterilized aqueous solution form, is then added to the ballmill container. Sterilized glass balls are then added to the container and the contents of the container are milled aseptically at 225 rpm for 16 hours, or until all particles are in the range of approximately 5 microns.

Under aseptic conditions, the micronized drug suspension formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 6

Formulation for oral administration:
Tablet
10–1000 mg each of a A-seco steroid with inactive ingredients such as starch, lactose and magnesium stearate can be formulated according to procedures known to those skilled in the art of tablet formulation.

EXAMPLE 7

Formulation for sterile intraocular injection:

| Component | each mL contains: |
| --- | --- |
| A-seco steroid | 10–100 mg |
| Sodium Chloride | 7.14 mg |
| Potassium Chloride | 0.38 mg |
| Calcium chloride dihydrate | 0.154 mg |
| Magnesium chloride hexahydrate | 0.2 mg |
| Dried sodium phosphate | 0.42 mg |
| Sodium bicarbonate | 2.1 mg |
| Dextrose | 0.92 mg |
| Hydrochloric acid or sodium hydroxide | q.s., pH to approx. 7.2 |
| Water for injection | q.s. |

EXAMPLE 8

Preferred formulation for a topical ocular solution:

| Component | wt. % |
| --- | --- |
| A-seco steroid | 0.005–5.0% |
| Benzalkonium chloride | 0.01% |
| HPMC | 0.5% |
| Sodium chloride | 0.8% |
| Sodium phosphate | 0.28% |
| Edetate disodium | 0.01% |
| NaOH/HCl | q.s. pH 7.2 |
| Purified Water | q.s. 100 mL |

EXAMPLE 9

A preferred formulation for oral administration:
Tablet
5–100 mg each of a A-seco steroid with inactive ingredients such as starch, lactose and magnesium stearate can be formulated according to procedures known to those skilled in the art of tablet formulation.

EXAMPLE 10

Formulations for topical dermatological use:
Cream
1 mg/g of a A-seco steroid in cream base of purified water, emulsifing wax, propylene glycol, stearic acid, isopropyl palmitate, synthetic beeswax, polysorbate 60, potassium sorbate, sorbic acid, propyl gallate, citric acid, and sodium hydroxide.
Ointment
1 mg/g each of a A-seco steroid in base of mineral oil and polyethylene.

EXAMPLE 11

Formulation for suppository:
10–500 mg each of a A-seco steroid with the following inactive ingredients: glycerin, butylateal hydroxytoluene, butylated hydroxyanisole, edetic acid, polyethylene glycol, and sodium chloride.

What is claimed is:

1. A method for treating opthalmic pathological neovascularization comprising administering to a human a composition comprising an effective amount of one or more A-seco steroids of formula (I)

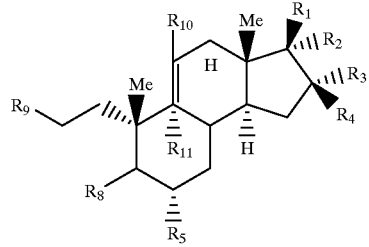

(I)

wherein:

$R_1$ is OH, OC(=O)$R_7$, $R_7$, C(=O)$R_7$, or C(=O)CH$_2$OR6;

$R_2$ is H, OH, OC(=O)$R_7$, CH$_3$, CH$_2$CH$_3$, C≡CH, or $R_2$ is combined with $R_3$ to form a cyclic acetonide;

$R_3$ is H, CH$_3$, OH, OC(=O)$R_7$, or $R_3$ may be combined with $R_2$ to form a cyclic acetonide;

$R_4$ is H or CH$_3$, with the proviso that if $R_4$ is CH$_3$ then $R_3$ is H;

$R_5$ is H, F or CH$_3$;

$R_6$ is H, C(=O)$R_7$, P(=O)(OH)$_2$ or a salt thereof;

$R_7$ is $C_1$ to $C_8$ alkyl, branched alkyl, cycloalkyl, or haloalkyl;

$R_8$ is (=O), OH or OC(=O)$R_7$ and may be in the α or β configuration, or $R_8$ may be combined with $R_9$ to form a lactone;

$R_9$ is C≡CH, C(=O)CH$_3$, COOH, COOR$_7$, CH$_2$OH, CH$_2$OC(=O)$R_7$, CONH$_2$, CONHR$_7$, CONR$_7$R$_7$, or $R_9$ may be combined with $R_8$ to form a lactone;

$R_{10}$ is H, (=O) or OH, or OC(=O)$R_7$ which may be in the α or β configuration, or, may be combined with $R_{11}$ to form a double bond; and $R_{11}$ is H, Cl, F, or may be combined with $R_{10}$ to form a double bond; in a pharmaceutically acceptable vehicle.

2. A method according to claim 1, wherein:

$R_1$ is C(=O)CH$_2$OR$_6$;

$R_2$ is OH;

$R_3$ is H;

$R_4$ is H;

$R_5$ is H;

$R_6$ is C(=O)$R_7$;

$R_7$ is CH$_3$;

$R_8$ is (=O);

$R_9$ is $COOR_7$;

$R_{10}$ is OH and in the β configuration or with $R_{11}$ forms a double bond; and $R_{11}$ is H, or combined with $R_{10}$ forms a double bond.

3. A method according the A-seco steroid is methyl A-seco-4-nor-21-acetoxy-11β, 17α-dihydroxypregnan-5, 20-dione-3-carboxylate.

4. A method according to claim 1, wherein the A-seco steroid is methyl A-seco-4-nor-21-acetoxy-17α-hydroxypregn-9 (11)-en-5, 20-dione-3-carboxylate.

5. A method for treating ophthalmic pathological neovascularization or controlling intraocular pressure (IOP) comprising administering to a human a composition comprising an effective amount of one or more A-seco steroids of formula (I)

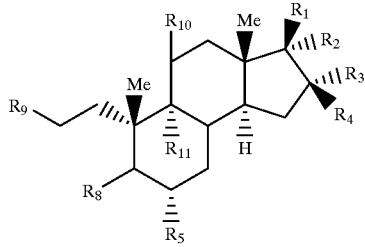

(I)

wherein:

$R_1$ is $C(=O)CH_2OR_6$;

$R_2$ is OH;

$R_3$ is H;

$R_4$ is H;

$R_5$ is H;

$R_6$ is $C(=O)R_7$;

$R_7$ is $CH_3$;

$R_8$ is (=O);

$R_9$ is $COOR_7$;

$R_{10}$ is OH and in the β configuration or with $R_{11}$ forms a double bond; and $R_{11}$ is H, or combined with $R_{10}$ forms a double bond; in a pharmaceutically acceptable vehicle.

6. A method according to claim 5, wherein the A-seco steroid is methyl A-seco-4-nor-21-acetoxy-11β,17α-dihydroxypregnan-5, 20-dione-3-carboxylate.

7. A method according to claim 5, wherein the A-seco steroid is methyl A-seco-4-nor-21-acetoxy-17α-hydroxypregn-9 (11)-en-5, 20-dione-3-carboxylate.

* * * * *